(12) United States Patent
Merril et al.

(10) Patent No.: US 7,521,479 B2
(45) Date of Patent: Apr. 21, 2009

(54) METHODS OF TREATING PRION DISEASE IN MAMMALS

(75) Inventors: Carl R. Merril, Bethesda, MD (US); Hossein A. Ghanbari, Potomac, MD (US)

(73) Assignees: Panacea Pharmaceuticals, Inc., Gaithersburg, MD (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/835,537

(22) Filed: Apr. 16, 2001

(65) Prior Publication Data

US 2002/0150631 A1    Oct. 17, 2002

(51) Int. Cl.
*A01N 37/52* (2006.01)
*A61K 31/155* (2006.01)

(52) U.S. Cl. .................................... 514/634
(58) Field of Classification Search ................ 424/671
See application file for complete search history.

(56) References Cited

U.S. PATENT DOCUMENTS

| | | | | |
|---|---|---|---|---|
| 5,385,946 | A | * | 1/1995 | Keana et al. ............... 514/634 |
| 5,403,861 | A | * | 4/1995 | Goldin et al. ............... 514/634 |
| 5,462,753 | A | * | 10/1995 | Bhatta ......................... 424/670 |
| 5,750,361 | A | | 5/1998 | Prusiner et al. |
| 5,948,763 | A | | 9/1999 | Soto-Jara et al. |
| 5,962,669 | A | | 10/1999 | Prusiner et al. |
| 6,020,537 | A | | 2/2000 | Prusiner |
| 6,060,293 | A | | 5/2000 | Bohr et al. |
| 2002/0132268 | A1 | * | 9/2002 | Chang et al. ............... 435/7.1 |
| 2004/0054006 | A1 | * | 3/2004 | Kaddurah-Daouk et al. 514/565 |

FOREIGN PATENT DOCUMENTS

| | | | |
|---|---|---|---|
| GB | 2315672 | * | 2/1998 |
| WO | WO9603425 | | 2/1996 |
| WO | WO-0048003 | * | 8/2000 |
| WO | 0076495 | * | 12/2000 |

OTHER PUBLICATIONS

Pocchiari et al, Combination of ultrafiltration and 6 M urea treatment of human growth hormone minimizes risk of CJD disease from potential CJD virus contamination, 1991, Hormone Research, 35 (3-4), 161-6.*
Manuelidis et al, Viral particles are required for infection in neurodegenerative CJD, 1995, Proceedings of the National Academcy of Sciences of USA, 92 (1), 5124-8.*
Madec et al, Biochemical properties of protease resistant prion protein PrPsc in natural sheep scrapie, 1997, Archives of Virology, 142(8), 1603-1612.*
Collinge et al., Nature, vol. 383(6602), pp. 685-690 (1996).
Partridge et al., Nature, vol. 407, pp. 457-458 (Sep. 2000).
True et al., Nature, vol. 407, pp. 477-483 (Sep. 2000).
Serio et al., Annu. Rev. Cell Dev. Biol., vol. 15, pp. 661-703 (1999).
Caspi et al., J. Biiol. Chem., vol. 273(6), pp. 3484-3489 (1998).
Prusiner et al., PNAS USA, vol. 95, pp. 13363-13383 (1998).
Weissmann, Charles, J. Biol. Chem., vol. 274 (1), pp. 3-6 (1999).
Wickner, Reed B., Science, vol. 264, pp. 566-569 (1994).
http://www.mnwelldir.org/docs/cancer1/altthrpy.htm p. 56 of 59.
http://www.ki4u.com, pp. 1-15 http://www.ki4u.com, pp. 1-15.
http://www.nlm.nih.gov/medlineplus/druginfo/sodiumiodidesystemic202621.html, pp. 1-6.
http://informatics.drake.edu/pth/html/chapter/mono/j1059850.htm, pp. 1-2.
http://informatics.drake.edu/patch_f/html/chapter/mono/hf059850.htm, p. 1.
http://informatics.drake.edu/pated_f/html/chapter/mono/hf059850.htm, pp. 1-3.
http://www.emedicine.com/NEURO/topic181.htm, pp. 1-14.
Clare Thompson, Nature, vol. 409, Feb. 8, 2001, pp. 660-661.
Quirin Schlermeier, Nature, vol. 409, Feb. 8, 2001, pp. 658-659.
Caughy et al., J. of Virology, 71(5), pp. 4107-4110 (1997).
Mabbott et al., Nature Medicine, vol. 7, No. 4, pp. 485-487 (Apr. 2001).

* cited by examiner

*Primary Examiner*—Alton N Pryor
(74) *Attorney, Agent, or Firm*—M. Elisa Lane

(57) ABSTRACT

The invention is related to the treatment of prion-related diseases such as the transmissible spongiform encephalopathies (TSEs) in mammals by administering chaotropic agents to or inducing a hyperthermia state in the affected mammals.

14 Claims, No Drawings

METHODS OF TREATING PRION DISEASE IN MAMMALS

FIELD OF THE INVENTION

The invention is related to the treatment of prion-related diseases such as the transmissible spongiform encephalopathies (TSEs) in mammals by administering chaotropic agents to the affected mammals.

BACKGROUND OF THE INVENTION

The term "prion" was coined in 1982 by Stanley Prusiner when describing his findings on the causative agents of the transmissible spongiform encephalopathies: proteinaceous infectious particles that lack any nucleic acid. These agents are truly unprecedented in medical science as infectious pathogens that cause fatal neurodegenerative disorders through an entirely novel mechanism. While prions may present as infectious, genetic, or sporadic disorders, they all develop as a direct result of a biochemical modification to the prion protein (PrP) that is a normal constituent of all mammalian cells (Prusiner, S. B., *Proc. Natl. A cad. Sci. USA* 9513363-13383(1998)).

The earliest studies of scrapie pathogenesis demonstrated that the disease could be directly transmitted from one animal to another. The scrapie agent was originally believed to be a virus, but it has, unlike known animal or any other kind of viruses, many unique characteristics such as the extraordinarily long incubation period to disease, the noninflammatory degenerative abnormalities that developed in the brain, and the lack of any demonstrable virion particles by classical virological techniques. The long incubation periods of the scrapie agent sets them apart from most viral infections. The complete absence of a detectable immune response is puzzling but this may now be explained by the fact that the agent may be a modified host protein. PrP is a host-specific protein, encoded by a single exon of a unique host gene. PrP is the product of highly conserved gene found in diverse organisms, and is a membrane bound protein thought to have an important, but yet unknown function.

Brains of scrapie-infected hamsters contain two forms of PrP: the cellular PrP ($PrP^C$) and the scrapie PrP ($PrP^{Sc}$) isoforms. Both proteins have a mass of 33-35 KD but they have different physical properties. $PrP^C$ is anchored to the cell surface and can be solubilized with ionic detergents as well as being susceptible to proteolytic agents. In contrast, $PrP^{Sc}$ cannot be solubilized by ionic detergents and looses only an amino-terminal peptide to proteolytic agents to yield a protein of mass 27-30 KD called PrP 27-30 (Prusiner et al. *Cell* 38:127-140(1994)).

PrP 27-30 is the major constituent of the pathognomonic amyloid plaques that are found in the brains of many hosts with spongiform encephalopathies. The quantity of this novel protein correlated with the titer of prion infectivity in brain. Moreover, PrP 27-30 was absent from uninfected brain, and it was found that various procedures that denatured, hydrolysed, or modified PrP 27-30 also inactivated prion infectivity.

No differences in the primary structure (i.e. amino acid sequence) of $PrP^C$ and $PrP^{Sc}$ have been detected, nor have any differences been found between PrP genes or mRNAs from normal and infected brains with respect to structure or copy number. The physical differences such as three-dimensional configuration between the two proteins are therefore attributed to post-translational chemical modification. In general, during the refolding of $PrP^C$ into $PrP^{Sc}$, some of the normal α-helical protein structure is partially converted into β-sheet.

To describe the nature of scrapie agent, two hypotheses were proposed: 1) a "protein only" hypothesis, in which the prion particle is devoid completely of nucleic acid; and 2) a "nucleoprotein or virino" hypothesis, in which the prion consists of a small nucleic acid and host-encoded protein. Sparrer et al.'s experiments suggest that protein only hypothesis is correct by using a yeast prion-like system (Sparrer H. E. et al. *Science* 289, 595 (2000)).

The recent pathogenesis studies of bovine spongiform encephalopathy have shown that experimentally infected cattle can show prion infectivity in the ileum (small intestine) in advance of their neurologic disease (Collee et al., *Lancet* 349:636-640 (1997)). Epidemiologic data now support an oral route of transmission in a number of animal prion disease outbreaks, although how sporadic prion diseases, such as Creutzfeldt-Jakob disease in humans, develop still remains unknown. Nevertheless, the fact that brain tissue from an affected host can transmit disease to an unaffected recipient (particularly if such material is inoculated directly into the brain of that recipient) now stands as one of the defining characteristics of all prion diseases. In addition, it has become clear that scrapie can induce disease in rodents following either a peripheral (subcutaneous, intraperitoneal, and oral) or an intracerebral inoculation.

It was reported that prion neuroinvasion requires B lymphocytes (Klein M A et al. *Nature* 390:687-690 (1997)). Almost paradoxically, normal PrP expression is not required for B cells to transmit disease to the brain, suggesting either that other cell type(s) whose maturation depends on B cells or their products (such as follicular dendritic cells) may promote neuroinvasion, or that B cells carry prions to the nervous system in a PrP-independent manner (Klein M A et al. *Nature Med* 4:1429-1433 (1998)).

In initial experiments, it was demonstrated that a prion disease in one species could be transferred to another. However, subsequent attempts at cross-species transmission were inconsistent. Recently, it has become clear that the successful passage of prions between species is almost always characterized by a prolonged incubation period during the first passage in the new host.

This time delay is often referred to as the prion "species barrier." However, on the next passage into a homologous host, the incubation period shortens and remains remarkably constant for all subsequent passages in that species. The species barrier occurs because new prions synthesized de novo in an experimentally inoculated host are generated from, and therefore reflect the protein sequence of, the host PrP and not that of the $PrP^{Sc}$ molecules in the inoculum (Bockman J M et al. *Ann Neurol.* 21:589-595 (1987)). Thus, the prion donor is the last mammal in which the prion was passaged and its PrP sequence represents the "species" of the prion.

The prion species is differs from the prion "strain" whose information appears to be enciphered in the conformation of the nascent $PrP^{Sc}$. Both the species and strain influence the ability of a given prion to cause symptomatic disease in a heterologous host. The species barrier concept is of practical importance in assessing the risk that humans may develop a prion disease after consuming scrapie-infected lamb or bovine spongiform encephalopathy-infected beef.

In yeast, two notable prion-like determinants [URE3] and [PSI], have been described (Reed B. Wickner, *Science* 264, 566-569 (1994); Wickner et al., *J. Biol. Chem* 274(2), 555-558 (1999)). Interestingly, different strains of yeast prions have been identified. Conversion to the prion-like [PSI] state in yeast requires the molecular chaperone Hsp 104; however, no homolog of Hsp 104 has been found in mammals (Patino, M. M et al., *Science* 273, 622-626(1996)). The $NH_2$ terminal prion domains of Ure2p and Sup35 that are responsible for the [URE3] and [PSI] phenotypes in yeast have been identified. In contrast to PrP, which is a GPI-anchored membrane protein, both of Ure2p and Sup35 are cytosolic proteins (Reed B. Wickner,. *Proc. Natl. Acad. Sci. USA* 94, 10012-10014 (1997)).

There have been efforts to provide treatment of prion diseases. For example, Tomiyama et al. disclose that antibiotic, rifampicin and its derivatives, which possess a naphthohydroquinone or naphthoquinone structure, inhibited Aβ1-40 aggregation and neurotoxicity in a concentration-dependent manner. Hydroquinone, p-benzoquinone and 1,4-dihydroxynaphthalene also inhibit Aβ1-40 aggregation and neurotoxicity at comparable molar concentrations to rifampicin (Tomiyama et al. *JBC* 271 (12): 6839-6844 (1996)).

Caspi et al. showed anions such as Congo red(CR) reduce the accumulation of $PrP^{Sc}$ in a neuroblastoma cell line permanently infected with prions as well as to delay disease onset in rodents when administered prophylactically.(Sigal Caspi et al., The Anti-prion Activity of Congo Red, *The Journal of Biological Chemistry,* 273(6), 3484-3489 (1998)).

DE 4229805 discloses that toxic effects displayed by $PrP^{Sc}$ and its peptide fragment can be blocked by antagonists of N-methyl-D-aspartate (NMDA) receptor channels, like Memantine. Flupirtine, a non-opiod analgesic drug, which is already in clinical use, was found to display in vitro a strong cytoprotective effect on neurons treated with $PrP^{C}$ or PrP106-126.

WIPO International Patent Publication No. WO0009111 discloses treatments of amyloidogenic diseases and prion diseases associated with conversion of protease sensitive PrP (PrP-sen) to protease resistant PrP(PrP-res) by administering tetrapyrrole such as phthalocyanines, deuteroporphyrins and meso-substituted prophines.

DE 4330388 discloses a curing or prevention of AIDS or mad cow disease by using L-tryptophan, indole, 3-indolylacetic acid or indomethacin to increase indole levels.

U.S. Pat. No. 5,935,927 to Vitek et al. teaches a method for stimulating amyloid removal in amyloidogenic diseases using advanced glycosylation endproducts to increase the activity of scavenger cells within the body at recognizing and removing amyloid deposits from affected tissues and organs.

U.S. Pat. No. 6,020,537 to Prusiner discloses prion protein standards for use as reference materials for prion detection and methods for the preparation of the prion protein standard. U.S. Pat. No. 5,962,669 to Prusiner describes a protein designated Prion Protein Modulator Factor (PPMF), which is an auxiliary factor in prion replication.

U.S. Pat. No. 5,750,361 discloses a method of screening for compounds which inhibits the binding of $PrP^{Sc}$ to a PrP peptide based on the fact that $PrP^{Sc}$ an increased β-sheet content, a diminished aqueous solubility, and a resistance to proteolytic digestion, relative to $PrP^{C}$.

U.S. Pat. No. 5,948,763 to Soto-Jara et al. discloses peptides capable of interacting with a hydrophobic structural determinant on a protein or peptide for amyloid or amyloid-like deposit formation inhibit and structurally block the abnormal folding of proteins and peptides into amyloid or amyloid-like deposits.

References in the art of treatment of prion diseases are scarce. Recently, U.S. Pat. No. 6,060,293 to Bohr et al. proposes treating prion related diseases by changing the functionality of the three-dimensional structure of proteins by applying high frequency energy having maximum frequency in the range of 0.01-100 GHz to a fluid system containing such proteins. However, it is not clear from the '293 patent how one would go about treating a mammal with such a disease.

Therefore, a need still exists for treating prion diseases, such as CJD and mad cow disease.

SUMMARY OF THE INVENTION

The present invention is directed to the treatment of prion diseases by administering protein denaturing agents, or chaotropic agents, to the affected mammal. The prion disease may be any of the transmissible spongiform encephalopathies known to infect various mammals, including humans.

DETAILED DESCRIPTION OF THE INVENTION

The present invention is based on the following observations. Evidence that certain neurodegenerative diseases such as the subacute spongiform encephalopathies (or transmissible spongiform encephalopathies) which include Creutzfeldt-Jakob disease (in humans), mad cow disease (in cows) and scrapie (in sheep) are due to prion proteins ($PrP^{Sc}$) has taken some time for the scientific community to accept. Prion proteins associated with disease appear to be more proteinase-resistant than the normal cellular prion protein ($PrP^{C}$). There is evidence that the proteinase-resistance and disease causing aspects of these proteins is due to abnormal structural conformations in the disease associated prion proteins ($PrP^{Sc}$). $PrP^{Sc}$, which has been found in diseased tissue and infectious material appears to be associated with the conversion of $PrP^{C}$ to $PrP^{Sc}$. It is this action that makes $PrP^{Sc}$ "infectious."

Given that normal cellular tissues contains prion protein ($PrP^{C}$) and that the abnormal form of the protein is due to an abnormal structural conformations one can assume that the normal structural conformation ($PrP^{C}$) is in a lower energy state than the disease causing state ($PrP^{Sc}$). If this were not the case we would all be affected with subacute spongiform encephalopathies, which we are not.

There are known mutations in the prion protein ($PrP^{C}$) that are associated with early onset of spongiform encephalopathies. In these cases, the energy state for prion formation may be lower or closer to that of the normal state. If it were lower than the normal state, one might expect death during embryogenesis. However, these mutations are rare. If the assumption that the normal structural conformation ($PrP^{C}$) is in a lower energy state than the disease causing state ($PrP^{Sc}$) is correct, then it may be possible to perturb the abnormal structural conformation of the $PrP^{Sc}$ prion proteins so that they can drop to the lower energy level of the normal cellular prion proteins ($PrP^{C}$), and thereby cure the disease state associated with the abnormal forms of the prion proteins.

Such perturbations can be caused by the action of chaotropic agents that interfere with and break down noncovalent bonds. Similarly chaotropic ions such as $I^{-}$ and $Br^{-}$ act by disrupting hydrophobic bonds near the surface of proteins.

In this regard it is interesting to note that an epigenetically inherited protein condition in yeast, which is capable of being propagated indefinitely, and is caused by a conformationally altered protein, can be "cured" by transient growth on guanidine-containing medium (Helmut E. Sparrer, Alex Santoso, Francis C. Szoka Jr., and Jonathan S. Weissman (2000) Evidence for the Prion Hypothesis: Induction of the Yeast [PSI+] Factor by in Vitro-Converted Sup35 Protein, Science 289: 595-599.).

Thus, the present invention is directed to a method of treating a prion disease in a mammal, which comprises administering a prion protein denaturing effective amount of a chaotropic agent to the mammal. By "denaturing" is meant that the agent will convert $PrP^{Sc}$ to the normal cellular form, $PrP^C$, or prevent the conversion of $PrP^C$ to $PrP^{Sc}$.

In the present application, the term of "cellular type of prion protein $PrP^C$" or "$PrP^C$" is used to indicate prions in their normal state and includes the naturally occurring one and its variants. The term of "scrapie type of prion protein $PrP^{Sc}$" or "$PrP^{Sc}$" means the cellular type protein which has undergone a three-dimensional structure change to have increased β-sheet structure, decreased solubility and proteolytic resistance when comparing with its normal state. The term "prion protein aggregates" means a complex formed between $PrP^C$ and a $PrP^{Sc}$.

By "prion diseases" is meant those disorders associated with or caused by the conversion of $PrP^C$ into $PrP^{Sc}$ or the consequent aggregation of prion proteins. It is sometimes used interchangeably with TSE (transmissible spongiform encephalopathies) or spongiform encephalopathies, herein. Examples of prion diseases contemplated in the present invention include: scrapie (sheep and goats); transmissible mink encephalopathy; chronic wasting disease (mule deer and elk); bovine spongiform encephalopathy (BSE); spongiform encephalopathy of exotic ruminants (nyala, gemsbok, Arabian oryx, eland, kudu, scimitar-horned oryx, ankole, and bison); feline spongiform encephalopathy (domestic cat, puma, cheetah, ocelot, tiger); Kuru; Creutzfeldt-Jakob disease, or CJD, which can be sporadic, familial or iatrogenic; Fatal Familial Insomnia (FFI); Gerstmann-Straussler-Scheinker (GSS) syndrome; and new variant Creutzfeldt-Jakob disease (nvCJD).

In the first aspect of the present invention, a chaoptropic agent is administered to the diseased mammal. By "administration" is meant any means of administration that accomplishes the application or delivery of the chaotropic agent to the affected tissues, and includes oral, nasal, parenteral, etc.

By "chaotropic substance" is meant any substance capable of altering the secondary, tertiary and/or quaternary structure of proteins and nucleic acids, but leaving at least the primary structure intact. While any chaotropic agent tolerated by a mammal can be used, preferred examples are a guanidine salt, sodium iodide, potassium iodide, urea or combinations thereof. More preferred are guanidine hydrochloride, potassium iodide, and urea, or combinations thereof. Most preferred is guanidine hydrochloride (also known as carbamidine hydrochloride and iminourea hydrochloride), which has been used in the therapy of LEMS.

The term "treatment" or "treating" and the like are used herein to generally mean obtaining a desired pharmacological and/or physiological effect. The effect may be therapeutic in terms of a partial or complete cure for a disease and/or adverse effects attributable to the disease. Thus, for example, it may indicate that (1) any symptoms of disorders associated with or caused by the conversion $PrP^C$ into $PrP^{Sc}$ or the consequent aggregation of prion proteins are reduced or alleviated by administration of the agents according to the present invention; or (2) $PrP^{Sc}$ is converted into $PrP^C$ by administration of the agents according to the present invention.

The term of "effective amount" is intended to mean that amount of an agent that, when administered to a mammal in need of such treatment, is sufficient to effect treatment for a disease in associated with aggregation of prion protein. Thus, e.g., a therapeutically effective amount of a prion protein denaturing agent such as guanidine hydrochloride in a quantity sufficient to modulate, regulate, or inhibit the conversion of $PrP^C$ into $PrP^{Sc}$ or the consequent aggregation of prion protein, or to promote the conversion of $PrP^{Sc}$ into $PrP^C$ or disintegrate the prion protein aggregates. The term "denaturing" means the conversion of $PrP^{Sc}$ into $PrP^C$ or its consequent disintegration of prion protein aggregates.

Guanidine hydrochloride is already used in the treatment of the neuromuscular condition called Lambert-Eaton myasthenic syndrome (LEMS). LEMS is a disease in which the immune system makes antibodies against nerve endings where acetylcholine is released, causing fluctuating muscular weakness to occur. Guanidine hydrochloride, previously thought by many doctors to be too toxic for routine use, increases secretion of acetylcholine from the nerve endings and is therefore useful in the treatment of LEMS. While the side effects of this drug range from bone marrow depression to renal problems to cardiac arrhythmia, it is still useful to treat a prion disease which is invariably fatal. That is, the benefits of therapy outweigh the risks.

The exact dosage and regimen of guanidine hydrochloride is determinable on an individual basis by the skilled practitioner; however, one can use the guidelines already available for the treatment of LEMS. That is, an initial dose of 5-15 mg/kg/day (divided into 3 or 4 doses per day) is given orally to the patient or animal with the prion disease. The dose may be increased to as much as about 40 mg/kg/day, depending on clinical response. Treatment would continue for as long as necessary to achieve a clinically positive result, which is a complete recovery or a delay of onset of disease or of further pathology.

Potassium iodide was used in the 1840's for the treatment of syphilis and was amazingly effective, even on patients with later stages of the illness. In addition, potassium iodide and sodium iodide are used as dietary supplements and for avoiding damage to the thyroid by radioactive iodine. They may be taken orally or parenterally. Dosage will depend on age and weight. For sodium iodide, normal daily recommended intakes are from about 40 µg (for infants and children) to about 200 µg for breast-feeding females. See www.nlm.nih.gov/medlineplus/druginfo/sodiumiodidesystemic202621.html. It is expected that for the treatment of TSEs, the dosage will be higher and determinable by the skilled practitioner based upon the clinical picture.

Much higher doses are routinely used for prophylaxis in the event of a radioactive accident, about 130 mg potassium iodide daily, taken orally. See www.ki4u.com, Potassium Iodide Anti-Radiation Pill FAQ (Apr. 6, 2001). Even twice as much has a low adverse reaction rate. Therefore, it is foreseen that the dosage of potassium iodide for the treatment of a prion disease will be from about 130 to about 260 mg per day. The usual dosage course is 10 days for preventing radiation damage; however, it is foreseen that treatment in patients with TSEs the treatment course could be considerably longer, perhaps for the lifetime of the patient, depending on the clinical outcome.

Urea has also been used in humans as a diuretic. The usual dosage is about 1 to 2 g/kg/day, and is injected or, more typically, infused. For the treatment of prion disease, the maximum tolerated dose is foreseen as most effective, although this can be determined by the skilled practitioner on a case-by-case basis.

Guanidine hydrochloride, sodium and potassium iodide, and urea are the preferred chaotropic agents for the treatment of prion-related diseases of the present invention, primarily because their use in humans and animals has been established. Other chaotropic agents which are safe for administration are also contemplated, however, for the present invention. Also, these compounds are chosen for their protein denaturing abilities, not for the diseases and conditions for which they are currently used in medicine. Therefore, the doses and treatment schedule may differ from that now used, and it is contemplated that for the denaturing effect on PrP$^{Sc}$ the maximum tolerated dose will ultimately be the most helpful in treating the disease.

The treatment of prion-related disease according to the present invention may be enhanced by increasing the body temperature. This can be attained through the use of hyperthermia or "fever therapy". By "hyperthermia" is meant the application of heat by external devices, such as thermal blankets, lasers, microwaves, etc. By "fever therapy" is meant internal heat therapy, i.e., by injection to the mammal of fever causing substances, or pyrogens. For example, in the late 19$^{th}$ century, William B. Coley used bacterial toxins to induce fever in bone cancer patients, which led to a surprising cure rate for inoperative patients. See Coley, William B, "A preliminary note on the treatment of inoperable sarcoma by the toxic product of erysipelas." *Post-Graduate* *:278-286 (1893), and Coley, William B., "The cancer symposium at Lake Mohonk." *Amer. J. Surg.* (New Series) 1:222-225 (1926). Recently, hyperthermia and fever therapy have been used in conjunction with radiation for the treatment of cancer. Fever therapy is effected by injecting the mammal with what are referred to as "mixed bacterial toxins" (Coley's toxins). See Havas et al. Cancer Res. 18:141-148(1958), which is incorporated herein by reference. A more preferred approach, however, is to use a microwave device to internally heat the patient to an acceptable level for a period of time determinable by the practitioner on an individual basis. Such a microwave device can be an MRI instrument, or other source. This heat therapy used in conjunction with the administration of chaotropic agent(s) is believed to enhance the action of the chaotropic substance and thereby shorten the length of therapy or reduce the dosage of the agent. Chaotropic agents generally work better at denaturing proteins when heat is applied.

This invention is further illustrated by the examples set forth below. The examples are to aid in a understanding of the invention but are not intended to, and should not be construed to, limit in any way the invention as set forth in the claims.

EXAMPLES

Example 1

Guanidine Hydrochloride Treatment in a Mouse Scrapie Model

This experiment would be performed using C57BL mice and scrapie strain ME7 as the model system, as described in, inter alia, Mabbott et al., *Nature Medicine* 7(4):485-487 (April 2001). The C57BL mice are divided into 6 groups: (a) control, no inoculation of ME7 (n=6); (b) control, inoculation with ME7, no treatment (n=6); (c) control, no inoculation of ME7, treatment with guanidine hydrochloride (n=6); (d) test, inoculation with ME7, treatment with guanidine hydrochloride (n=6); (e) control, no inoculation with ME7, treatment with guanidine hydrochloride at one day post inoculation; and (f) test, inoculated with ME7, treatment with guanidine hydrochloride one day post inoculation. All mice are 6-8 weeks of age. Groups b, d and f are inoculated intraperitoneally with 20 μl of a 1.0% (wt/vol) suspension of uncentrifuged brain homogenate from ME7 scrapie-infected mice. The group a, c and e mice are given an i.p. injection of PBS as control.

It has been observed that at 70 days post-infection, high levels of infective agent and PrP$^{Sc}$ are known to accumulate in lymphoid tissue. See Mabbott et al., supra. At 70 days post-infection, therefore, treatment is initiated on the mice in groups c and d. At the same time, 2 mice from each group are sacrificed, and the level of infectivity and level of PrP$^{Sc}$ are determined in a known manner (Mabbott et al., supra, which is incorporated herein by reference).

In the group e and f mice, treatment is initiated at one day post inoculation in order to determine if guanidine hydrochloride exhibits a prophylactic-like effect, i.e. whether it prevents the titer of PrP$^{Sc}$ from getting higher than the initial inoculum.

The treatment regimen would be the same as for treatment of LEMS with guanidine hydrochloride. That is, an initial dose of 15 mg/kg/day (divided into 3 doses per day in aqueous solution) is given orally to the mice in the treatment groups. After 7 days the dose is increased to 40 mg/kg/day for the remainder of life. The mice would be observed for clinical signs of disease, and the days post-infection recorded. A second endpoint to be observed is the time of death of all of the mice. At that time, the levels of infectivity and PrP$^{Sc}$ in the spleens will be determined.

It is expected that the mice in group d will live as long as the mice in group a to a statistical degree, even though titers of PrP$^{Sc}$ and infectivity would be statistically about the same as group b at 70 days post-inoculation. It is also expected that group d will have lower infectivity and lower PrP$^{Sc}$ titers than group b at the final endpoint of the study. In addition, it is expected that the of PrP$^{Sc}$ in group f will be either negligible or not much higher than that provided in the initial inoculum, which would show that guanidine hydrochloride is effective in preventing higher titers of the infective agent, $PrP^{Sc}$, from occurring. The results overall will indicate that guanidine hydrochloride is effective in the treatment of scrapie.

The invention is not intended to be limited by the foregoing example, but is defined by the appended claims and their equivalents.

We claim:

1. A method of treating a prion disease in a mammal, comprising selecting a mammal that is suffering from a prion disease, and administering an effective amount of a guanidine salt to the mammal.

2. The method according to claim 1, wherein said guanidine salt is guanidine hydrochloride.

3. The method of claim 1, wherein the prion disease is transmissible spongiform encephalopathy.

4. The method according to claim 1, wherein said prion disease is scrapie, transmissible mink encephalopathy, chronic wasting disease, bovine spongiform encephalopathy, spongiform encephalopathy of exotic ruminants, feline spongiform encephalopathy, kuru, Creutzfeldt-Jakob disease (CJD), fatal familial insomnia, Gerstmann-Straussler-Scheiniker syndrome, or new-variant Creutzfeldt-Jakob disease (nvCJD).

5. The method according to claim 4, wherein said mammal is human, cow, sheep, mink, or cat.

6. The method according to claim 1, wherein said prion disease is bovine spongiform encephalopathy.

7. The method according to claim 6, wherein said mammal is a cow.

8. The method according to claim 1, wherein said prion disease is CJD or nvCJD.

9. The method according to claim 8, wherein said mammal is human.

10. The method of claim 1, further comprising inducing hyperthermia in said mammal during the course of treatment with the guanidine salt.

11. The method of claim 2, wherein between about 5 mg and about 40 mg per kilogram of guanidine hydrochloride is administered per day.

12. The method according to claim 10, wherein said hyperthermia is produced through applying microwave energy.

13. The method according to claim 10, wherein said hyperthermia is induced by administering pyrogenic material to the mammal.

14. The method according to claim 13, wherein said pyrogenic material is a mixture of inactivated bacterial toxins.

* * * * *